United States Patent
Lee et al.

(10) Patent No.: US 11,578,045 B2
(45) Date of Patent: Feb. 14, 2023

(54) FURAN MONOMER HAVING BIFUNCTIONAL HYDROXYMETHYL GROUP AND PREPARATION METHOD THEREFOR

(71) Applicant: Kukdo Chemical Co., Ltd., Seoul (KR)

(72) Inventors: Shin Youp Lee, Seoul (KR); Chan Ho Park, Seoul (KR)

(73) Assignee: KUKDO CHEMICAL CO., LTD, Seoul (KR)

( * ) Notice: Subject to any disclaimer, the term of this patent is extended or adjusted under 35 U.S.C. 154(b) by 120 days.

(21) Appl. No.: 16/492,552

(22) PCT Filed: Jan. 18, 2018

(86) PCT No.: PCT/KR2018/000865
§ 371 (c)(1),
(2) Date: Sep. 9, 2019

(87) PCT Pub. No.: WO2018/174396
PCT Pub. Date: Sep. 27, 2018

(65) Prior Publication Data
US 2021/0139443 A1    May 13, 2021

(30) Foreign Application Priority Data
Mar. 20, 2017    (KR) .................. 10-2017-0034795

(51) Int. Cl.
*C07D 307/42*    (2006.01)
(52) U.S. Cl.
CPC .................. *C07D 307/42* (2013.01)
(58) Field of Classification Search
CPC .................................... C07D 307/42
See application file for complete search history.

(56) References Cited

U.S. PATENT DOCUMENTS

| 4,634,723 A | 1/1987 | Gardziella et al. |
| 2010/0062276 A1 | 3/2010 | Van Rhijn |

FOREIGN PATENT DOCUMENTS

| JP | 60-223858 A | 11/1985 |
| JP | H08-506374 A | 7/1996 |
| JP | 2000-246391 A | 9/2000 |
| JP | 2002-080408 A | 3/2002 |
| JP | 2002-80408 A | 3/2002 |
| JP | 2013-095859 A | 5/2013 |
| JP | 2013-95859 A | 5/2013 |
| JP | 2013095859 | * 5/2013 |
| KR | 10-1791852 B1 | 11/2017 |

OTHER PUBLICATIONS

JP2013095859-machine-translation, 2022, machine translation of description of JP2013095859.*
Roman-Leshkov, Yuriy, et al. "Production of dimethylfuran for liquid fuels from biomass-derived carbohydrates." Nature 447.7147 (2007): 982.
International Search Report received in PCT Application No. PCT/KR2018/000865, dated Apr. 23, 2018.
Iovel et al., "Hydroxymethylation of Furan and its Derivatives in the Presence of Cation-Exchange Resins*", Journal of Molecular Catalysis, vol. 57—13 pages (1989).
Boyer et al., "Rhodium-Catalyzed Domino Enantioselective Synthesis of Bicyclo[2.2.2]lactones", Angewandte Chemie, Supporting Information—43 pages (2011).
Extended European Search Report of Patent Application No. 18770224.6—9 pages (dated Aug. 4, 2020).
Office Action of Japanese Patent Application No. 2019-566551—3 pages (dated Oct. 6, 2020).

* cited by examiner

Primary Examiner — Sun Jae Yoo
(74) Attorney, Agent, or Firm — Knobbe, Martens, Olson & Bear, LLP

(57) ABSTRACT

The present disclosure relates to a method of preparing a furan monomer having a bifunctional hydroxymethyl group (2, 5-bis(hydroxymethyl) furan (BHMF)). The method includes converting furfuryl alcohol to a low-molecular weight furan mixture extracting and purifying the furan monomer having a bifunctional hydroxymethyl group from the low-molecular weight furan mixture.

9 Claims, 9 Drawing Sheets

Detector A Ch1

| Peak# | Ret. Time | Area | Height | Area % |
|---|---|---|---|---|
| 1 | 37.856 | 13054 | 641 | 1.223 |
| 2 | 38.311 | 54273 | 2367 | 5.083 |
| 3 | 38.871 | 177021 | 7400 | 16.579 |
| 4 | 39.545 | 431457 | 17580 | 40.409 |
| 5 | 40.391 | 391921 | 14783 | 36.706 |
| Total | | 1067725 | 42771 | 100.000 |

| Peak# | Ret. Time | Area | Height | Area % |
|---|---|---|---|---|
| 1 | 36.067 | 262999 | 2648 | 7.833 |
| 2 | 36.495 | 130220 | 3872 | 3.878 |
| 3 | 37.109 | 226883 | 5954 | 6.758 |
| 4 | 37.958 | 381476 | 12426 | 11.362 |
| 5 | 38.367 | 79996 | 4924 | 2.383 |
| 6 | 39.134 | 1714614 | 65219 | 51.066 |
| 7 | 39.829 | 171024 | 7550 | 5.094 |
| 8 | 40.634 | 385106 | 15066 | 11.470 |
| 9 | 41.566 | 5185 | 214 | 0.154 |
| Total | | 3357505 | 117874 | 100.000 |

| Peak# | Ret. Time | Area | Height | Area % |
|---|---|---|---|---|
| 1 | 36.562 | 137948 | 1583 | 4.853 |
| 2 | 37.377 | 98404 | 2839 | 3.462 |
| 3 | 38.156 | 235591 | 5071 | 8.288 |
| 4 | 39.253 | 2342697 | 93936 | 82.417 |
| 5 | 40.760 | 27859 | 1029 | 0.980 |
| Total | | 2842499 | 104458 | 100.000 |

| Peak# | Ret. Time | Area | Height | Area % |
|---|---|---|---|---|
| 1 | 36.574 | 779 | 28 | 0.025 |
| 2 | 37.245 | 750 | 24 | 0.024 |
| 3 | 38.219 | 5110 | 151 | 0.163 |
| 4 | 39.211 | 3128892 | 126930 | 99.688 |
| 5 | 41.101 | 3166 | 203 | 0.101 |
| Total | | 3138697 | 127336 | 100.000 |

FIG. 10
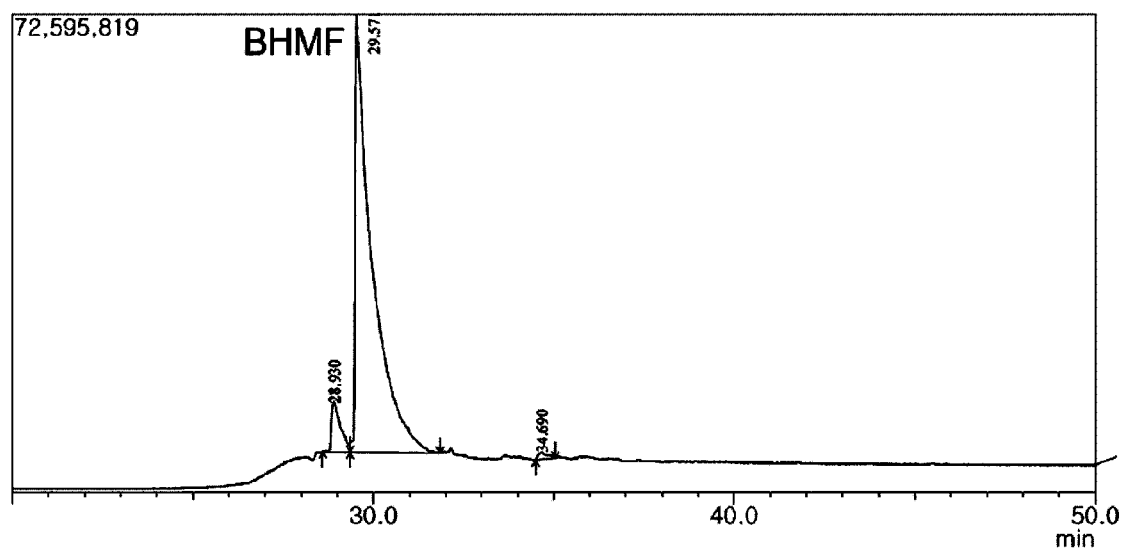
Peak Report TIC
| Peak# | R.Time | I.Time | F.Time | Area | Area% |
|---|---|---|---|---|---|
| 1 | 28.930 | 28.600 | 29.350 | 134941248 | 5.80 |
| 2 | 29.571 | 29.350 | 31.850 | 2173374359 | 93.39 |
| 3 | 34.690 | 34.500 | 35.050 | 19001786 | 0.82 |
|  |  |  |  | 2327317393 | 100.00 |
<< Target >>
Line#:2  R.Time:29.575(Scan#:3549)  MassPeaks:172
RawMode:Averaged 29.567-29.583(3548-3550) BasePeak:97.00(11551022)
BG Mode:Calc. from Peak
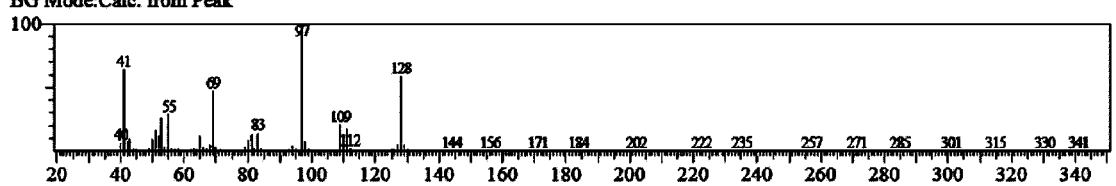

FURAN MONOMER HAVING BIFUNCTIONAL HYDROXYMETHYL GROUP AND PREPARATION METHOD THEREFOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is a U.S. national phase application of PCT/KR2018/000865 filed on Jan. 18, 2018 that claims the benefit of Korean Patent Application No. 10-2017-0034795, filed Mar. 20, 2017, each of which is incorporated by reference herein in its entirety.

BACKGROUND

Technical Field

The present disclosure relates to a furan monomer having a bifunctional hydroxymethyl group and a preparation method therefor. More particularly, the present disclosure relates to a furan monomer having a bifunctional hydroxymethyl group, which can be utilized as a raw material for polymers and as a furan monomer precursor, and a method for preparation thereof from biomass-derived furfuryl alcohol.

Background Art

In the face of the fact that petroleum resources are finite and the deterioration of environmental problems results from the use thereof, biomass resources have increasingly emerged thanks to the sustainability and eco-friendly advantage thereof. In this context, development of biomass-based monomer and polymer production techniques is considered as an important matter in both academic fields and industrial fields.

Among various bio-derived materials, a furan polymer is a material superior in terms of thermal resistance, acid resistance, and adhesiveness and is used as a thermosetting or acid-setting resin in the casting industry and in the adhesive field. A furan structure is produced by thermal decomposition of pentose or hexose into a furfural structure or hydroxymethyl furfural (HMF) structure, respectively.

Furan materials in current industrial use are limited, for the most part, to polymers mainly for the reason that the high reactivity of furan monomers invokes resinification, making it difficult to prepare furan in a monomer form. In the aspect of usage, furan materials that are high in crosslinking density and are resinified are needed for use as heat-resistant binder materials in the casting industry, which is the main application field thereof. For this reason, intensive research has been conducted into the synthesis of high-molecular weight furan polymers. In contrast, low-molecular weight furan monomers have not attracted commercial interests.

With the recognition of furan building blocks at a monomer level as important materials, studies have recently been conducted on furan monomers, centering around developed countries including the U.S.A., the Europe, and the like. Biomass-derived furan compounds provide various characteristics and properties discriminating from those of conventional petroleum-derived aromatic compounds and allow the production of furan monomers in purified forms, which may lead to the synthesis of various standardized furan polymers.

Representative of the studies is the development of 2, 5-furandicarboxylic acid (FDCA) monomer by Avantium, Netherland. This company succeeded in developing polyethylene furanoate (PEF), which is a FDCA-based polyester, with the aim of replacing conventional polyethylene terephthalate (PET) materials. PEF materials are known to exhibit a gas barrier property up to six times as high as that of PET.

Meanwhile, studies on the production of a 2, 5-bis(hydroxymethyl) furan (BHMF) monomer having a bifunctional hydroxymethyl group, which is applicable as a material for polymers such as epoxy resins, are ongoing. However, BHMF is too high in production cost to commercially apply and is now sold at high price in the reagent market (>10 $/g).

The reason of the current high production cost of BHMF is as follows: Conventional BHMF monomers can be acquired by reducing the precursor HMF derived from hexoses such as glucose, fructose, and the like. However, HMF is of poor storage because it is apt to easily convert into by-products such as levulinic acid, humain, etc. due to the low thermal and chemical stability thereof in an aqueous solution phase. Further, HMF, which has a boiling point of as high as 291° C. to 292° C. at atmospheric pressure, easily degrades upon distillation and thus is advantageous for high concentration/mass production. Consequently, current BHMF production techniques in which hexose-based HMF is isolated at high purity and then reduced are disadvantageous in terms of efficiency and economic feasibility. Some techniques, such as the biphasic reaction system (Nature, 2007, 447: 982), etc., have been suggested in order to solve the by-product production problem, but have encountered many barriers to commercialization because of low yield, restrictive catalyst use, complicate processes, etc.

SUMMARY OF CERTAIN INVENTIVE ASPECTS

Intensive and thorough research into economic and efficient synthesis method for BHMF monomers, conducted by the present inventors, with the aim of solving the foregoing problems, resulted in the finding that furfuryl alcohol other than HMF can be used as a precursor for production of BHMF, leading to the present disclosure concerning a production method comprising a hydroxymethylation process of furfuryl alcohol and a high-purification process of BHMF.

A method for producing a furan monomer having a bifunctional hydroxymethyl group (2, 5-bis(hydroxymethyl) furan (BHMF)) according to various embodiments of the present disclosure may comprise the steps of: using furfuryl alcohol to synthesize a low-molecular weight furan mixture; and extracting and highly purifying a furan monomer having a bifunctional hydroxymethyl group from the low-molecular weight furan mixture.

In various embodiments of the present disclosure, a furan monomer having a bifunctional hydroxymethyl group, such as BHMF, can be very easily synthesized using furfuryl alcohol based on a biomass-derived pentose. The BHMF production method according to various embodiments of the present disclosure is industrially valuable because the method utilizes an industrially highly accessible raw material in effectively producing BHMF. Subsequently, the method can play a critical role in commercializing various derived furan products using BHMF as a raw material. In the

BRIEF DESCRIPTION OF THE DRAWINGS

FIG. 10 shows GS-MS data of the highly pure BHMF prepared according to Example 3 in the present disclosure.

DETAILED DESCRIPTION OF CERTAIN INVENTIVE EMBODIMENTS

A method for producing a furan monomer having a bifunctional hydroxymethyl group (2, 5-bis(hydroxymethyl)furan (BHMF)) according to various embodiments of the present disclosure may comprise the steps of: using furfuryl alcohol to synthesize a low-molecular weight furan mixture; and extracting and highly purifying a furan monomer having a bifunctional hydroxymethyl group from the low-molecular weight furan mixture.

Hereinafter, a method for producing BHMF according to the present disclosure will be described in detail with reference to the following exemplary embodiments. At this time, the following description is not limited to particular embodiments of the present disclosure, it must be understood as including all of changes, equivalents, and substitutes included in the spirit and scope of the present disclosure. Also, various components used in the following detailed description are not limited to the described terms. In addition, all terms used herein, including technical terms and scientific terms, has the same meaning as commonly understood by those of ordinary skill in the art unless otherwise defined.

Hereinafter, detailed exemplary embodiments of the present disclosure will be described with reference to the accompanying drawings.

Figure 1:
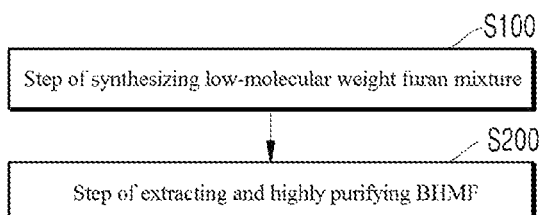
FIG. 1 is a flow diagram of a BHMF production method according to various embodiments of the present disclosure.

FIG. 1 is a flow diagram of a BHMF production method according to various embodiments of the present disclosure.

Referring to FIG. 1, the BHMF production method according to various embodiment of the present disclosure may comprise the steps of synthesizing a low-molecular weight furan mixture (S100); and extracting and highly purifying BHMF (S200).

In the step of synthesizing a low-molecular weight furan mixture (S100), furfuryl alcohol may be used to synthesize the low-molecular weight furan mixture. The raw material precursor furfuryl alcohol can be obtained typically by reducing furfural. In contrast to HMF, which is an expensive raw material for conventional BHMF production methods, furfural and furfuryl alcohol, which are raw material precursors for the method of the present disclosure, are produced on an industrial scale at low price (1,t $/ton-1,500 $/ton).

Furfural is produced by acid hydrolysis from lignocellulosic biomass and may be obtained by the acid-catalyzed dehydration of aldopentoses, particularly xylose. In this context, the final product BHMF may be a biomass-based furan monomer from which bio-derived polymers can be produced.

Biomass→Furfural→Furfuryl→alcohol→BHMF→Polymer

The main raw material furfuryl alcohol and its precursor furfural are commercialized products (annual production worldwide 400 thousand tons). Examples of the raw material biomass useful for production of furfuryl alcohol and furfural include agricultural by-products such as corncob and sugarcane bagasse. This is the point that is discriminated from the conventional BHMF production methods using HMF, which is produced mainly from edible crops (corn, potato, etc.). In this sense, a technique for producing furan monomers in which non-edible biomass is used as a starting material is eco-friendly.

The commercial application of furfuryl alcohol at the current technical level is limited to furan resins. Furan resins are utilized in various forms including furfuryl alcohol/urea-formaldehyde resin, furfuryl alcohol/formaldehyde resin, furfuryl alcohol/phenol/formaldehyde resin, and the like and may be used alone or in combination with a filler/supplement, depending on purposes. Because conventional furan resins aims to be of high corrosion resistance, chemical resistance, and thermal resistance, focus has been made on the synthesis of high-molecular weight furan polymers. There have been some examples of developing furan resins with a high low-molecular weight content. However, the resins is limited to the use of providing high-molecular weight furan resins with solubility and thus with compatibility with other resins. The production/purification of furfuryl alcohol-derived BHMF monomers alone as in the present discloses are not found previously.

Various embodiments of the present disclosure disclose an economical and effective BHMF monomer synthesis method by which BHMF can be produced using non-edible biomass- or waste biomass-derived furfuryl alcohol other than HMF, which is conventionally used.

Figure 2:
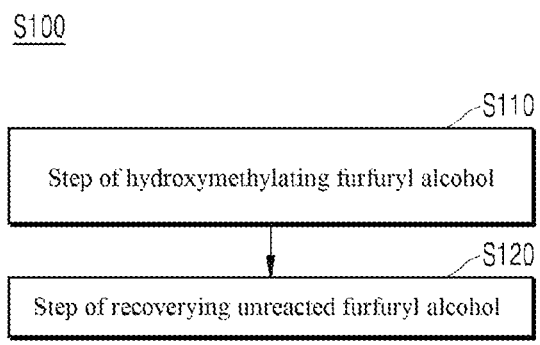
FIG. 2 is a flow diagram concretely explaining a step of synthesizing a low-molecular weight furan mixture in the BHMF production method according to various embodiments of the present disclosure.

FIG. 2 is a flow diagram concretely explaining the step of synthesizing a low-molecular weight furan mixture in the BHMF production method according to various embodiments of the present disclosure.

With reference to FIG. 2, the step of synthesizing a low-molecular weight furan mixture (S100) in the BHMF production method may include the steps of hydroxymethylating furfuryl alcohol (S110) and recovering unreacted furfuryl alcohol (S120).

In the step of synthesizing a low-molecular weight furan mixture (S100), the three side reactions of i) formation of levulinic acid, ii) Diels-Alder reaction, and iii) self-condensation can be controlled. That is, the step of synthesizing a low-molecular weight furan mixture (S100) can maximize the BHMF content with the minimization of the three side reactions. In the step of synthesizing a low-molecular weight furan mixture (S100), a maximum of BHMF contents and a minimum of side reactions can be achieved by i) inhibiting levulinic acid formation through the minimization of moisture content in the reactor, ii) minimizing a Diels-Alder reaction through the control of a reaction temperature range, and iii) minimizing self-condensation through acid catalyst selection and raw material composition ratio control. Greater details are given as follows.

In the step of hydroxymethylating furfuryl alcohol (S110), the raw material furfuryl alcohol, solid-phase formaldehyde, and an acid catalyst may be mixed together. The solid-phase formaldehyde may be, for example, paraformaldehyde. In the step of hydroxymethylating furfuryl alcohol (S110), monomeric formaldehyde resulting from thermal degradation of paraformaldehyde may combine with furfuryl alcohol. According to various embodiments of the present disclosure, the minimization of moisture content in the reactor and the inhibition of levulinic acid formation can be achieved by using paraformaldehyde as a hydroxymethylation material. Thus, an improvement can be brought about in the yield of BHMF and, in turn, in the separation efficiency of furan monomers in a subsequent process.

Typically, the hydroxymethylation reaction employs formalin, an aqueous solution of formaldehyde, as a raw material. Commercialized formalin is an aqueous solution of 30% to 35% by weight of low-molecular weight formaldehyde. The use of formalin is advantageous in terms of raw material control and feeding, but increases a moisture content in a reactor to generate a significant amount of levulinic acid as a by-product upon hydroxymethylation, giving rise to decreasing a reaction yield and a separation efficiency of furan monomers.

In the present disclosure, paraformaldehyde, which is a polymerized, solid-phase formaldehyde, is fed as a raw material and then thermally degraded into monomeric formaldehyde through the control of reaction temperatures, with the concomitant hydroxymethylation of furfuryl alcohol, thereby minimizing the moisture content in the reactor.

The step of hydroxymethylating furfuryl alcohol (S110) may be conducted at a temperature of 100° C. to 150° C. More particularly, the step may be conducted at a temperature of 100° C. to 120° C. In this condition, the Diels-Alder reaction can be minimized while the yield of BHMF can be improved. In detail, in case that the process temperature exceeds 150° C., a Diels-Alder reaction may be drastically induced upon BHMF synthesis using furfuryl alcohol, leading to gelation within several minutes. If occurring, gelation makes it impossible to proceed additional reactions and recover the product. At high temperatures, furfuryl alcohol undergoes a Diels-Alder reaction, which is further facilitated in the presence of an acid catalyst. When occurring simultaneously, the self-condensation and Diels-Alder reaction of furfuryl alcohol invokes drastic gelation, together heat generation, thus making the normal production of BHMF impossible. In contrast, a process temperature less than 100° C. may not activate decreased thermal degradation and hydroxymethylation of paraformaldehyde, thus decreasing production efficiency.

In the step of hydroxymethylating furfuryl alcohol (S110), the acid catalyst is an organic acid with a pKa of 3.0 to 6.4 and may be selected from the group consisting of acetic acid, acetoacetic acid, adipic acid, azelaic acid, benzoic acid, citric acid, cyclohexanecarboxylic acid, enolpyruvic acid, formic acid, fumaric acid, galactaric acid, galactonic acid, glucaric acid, gluconic acid, glutaric acid, glyceric acid, glyceric acid 2-phosphate, glycolic acid, glyoxylic acid, hydroxybutyric acid, isobutyric acid, isophthalic acid, itaconic acid, lactic acid, levulinic acid, malic acid, methyl malonic acid, pimelic acid, succinic acid, suberic acid, tartaric acid, terephthalic acid, monosodium succinate, disodium citrate, and a combination thereof. More particularly, the acid catalyst may be an acid with a pKa of 3.5 to 4.5. For example, succinic acid may be used as the acid catalyst. According to various embodiments of the present disclosure, delimitation of the pKa of the acid catalyst to 3.0 to 6.4 allows the suppression of unnecessary self-condensation while guaranteeing acidity sufficient enough to conduct hydroxymethylation. In consideration of the reaction mechanisms in which both the hydroxymethylation and the self-condensation are activated by an acid catalyst, it is impossible to achieve the complete exclusion of the self-condensation (the perfect removal of side reactions). In various embodiments of the present disclosure, the acid catalyst is controlled to retain a suitable acidity so that the hydroxymethylation predominates over the self-condensation.

In detail, an acid catalyst with a pKa of 2.0 or less may be unsuitable for the production of low-molecular weight furan monomers because self-condensation and Diels-Alder reactions are conducted very fast in the presence of the acid catalyst so that the synthesized products are, for the most part, polymerized. On the other hand, an acid catalyst with a pKa of higher than 6.4 provides an acidity insufficient to perform hydroxymethylation, resulting in a decreased reaction efficiency and a low output of BHMF relative to input raw materials and obtained by-products.

Meanwhile, an acid catalyst with a pKa of 3.0 to 6.4 may be contained in an amount of 0.05 phr to 0.3 phr relative to furfuryl alcohol. When an acid catalyst with a pKa of 3.0 to 6.4 is used in an amount less than 0.05 phr relative to furfuryl alcohol, the hydroxymethylation for producing a low-molecular weight furan mixture may be too slowly conducted. In addition, more than 0.3 phr of an acid catalyst with a pKa of 3.0 to 6.4 relative to furfuryl alcohol may increase amounts of by-products.

In the step of hydroxymethylating furfuryl alcohol (S110), the furfuryl alcohol may be mixed at a 2- to 30-fold greater molar ratio to formaldehyde. Particularly, the furfuryl alcohol may be mixed at a 6- to 15-fold greater molar ratio relative to formaldehyde. The ratio may contribute to setting a condition under which the production of BHMF relative to furan polymers can be maximized. In various embodiments of the present disclosure, minimum levels enough to conduct hydroxymethylation may be applied to the reaction temperature and catalyst activity so as to minimize the output of polymers. Meanwhile, a too long time of the reaction may afford a significant amount of by-products and may provoke that the already produced BHMF participates in additional polymerization and does not exist as a monomer anymore. In order to solve these problems, excess furfuryl alcohol relative to formaldehyde is fed such that BHMF is produced within as short as period of reaction time as possible, with the consequent reduction of the output of by-products, in various embodiment of the present disclosure. In addition, unreacted furfuryl alcohol can be simply recovered by vacuum distillation and can be reused. In detail, when furfuryl alcohol is fed at a molar ratio less than 2, only insufficient hydroxymethylation is performed so that a significant amount of residual formaldehyde exists, together with the problem of low yield. Application of a severe condition for encouraging entire formaldehyde to participate in the reaction may be accompanied by an inevitable increase of polymers. Although increasing BHMF productivity, molar ratio of more than 30 of furfuryl alcohol inevitably requires an increased volume of the reactor relative to the product and consumes much energy and time for recovering unreacted furfuryl alcohol, which is of no commercial use.

In the foregoing process condition, for example, the step of hydroxymethylating furfuryl alcohol (S110) may be conducted for two to eight hours. A process time less than two hours does not guarantee sufficient hydroxymethylation of furfuryl alcohol, resulting in a significant amount of residual formaldehyde and a decreased BHMF yield. When the process time exceeds eight hours, an increase may be brought about in a side reaction, a Diels-Alder reaction, and unnecessary self-condensation which lead to levulinic acid formation, gelation, and by-product formation, respectively.

The step of hydroxymethylating furfuryl alcohol (S110) may comprise a neutralization process. After a suitable process time, for example, a process time of two to eight hours, a neutralization process may be conducted to neutralize the acid catalyst. A neutralization material for the neutralization process may be, for example, NaOH. The amount of the neutralization material may vary depending on the input of the acid catalyst.

In the step of recovering unreacted furfuryl alcohol (S120), the furfuryl alcohol that has not participated in the reaction can be recovered after the step of hydroxymethylating furfuryl alcohol (S110). Following the neutralization process, for example, the step of recovering furfuryl alcohol (S120) may be conducted by cooling and dehydrating the reaction mixture, followed by vacuum distillation at 100° C. to 150° C. According to various embodiments of the present disclosure by-product output is reduced so that unreacted furfuryl alcohol can be simply through vacuum distillation and can be reused.

The low-molecular weight furan mixture synthesized through the step of synthesizing a low-molecular weight furan mixture (S100) may contain 50% or greater of furan polymers, including BHMF, having five or less furan ring repeat units. In addition, the BHMF obtained through the step of extracting and highly purifying BHMF (S200) may account for 50% or greater of furan polymers having two or less furan ring repeat units and a hydroxymethyl group at each of the opposite ends.

Figure 3:
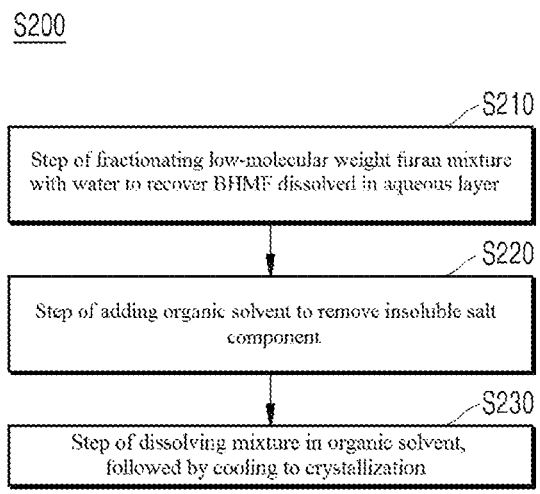
FIG. 3 is a flow diagram concretely explaining a step of extracting and highly purifying BHMF in the BHMF production method according to various embodiments of the present disclosure.

FIG. 3 is a flow diagram concretely explaining the step of extracting and highly purifying BHMF in the BHMF production method according to various embodiments of the present disclosure.

In the step of extracting and highly purifying BHMF (S200), highly pure furan monomers can be separated from the low-molecular weight furan mixture obtained in the step of synthesizing a low-molecular weight furan mixture (S100). In the low-molecular weight furan mixture obtained in the step of synthesizing a low-molecular weight furan mixture (S100), the target material BHMF coexists with residues after the neutralization of the acid catalyst, including catalyst acid salts, levulinic acid salts, and a trace of residual furfuryl alcohol, and a significant amount of furan oligomers (n=1, 2, 3, ...). In most cases, such impurities are found at various contents of 10% to 50%, and a total content of the impurities and ratios of individual impurities can be controlled depending on reaction conditions. In the step of extracting and highly purifying BHMF (S200), the impurities can be removed to highly purify BHMF.

With reference to FIG. 3, the step of extracting and highly purifying BHMF (S200) may comprise at least one of the steps of fractionating the low-molecular weight furan mixture with water to recover the BHMF dissolved in the aqueous layer (S210), adding an organic solvent to remove insoluble salt components (S220), and dissolving the mixture, followed by cooling the solution to crystallization (S230). Even when any one of these three steps is used alone, a significant effect can be brought about. When used together, two or more of the three steps can further enhance the high purification efficiency. In addition, the three steps can be applied sequentially, but the embodiments of the present disclosure are not limited thereto.

In the step of fractionating the low-molecular weight furan mixture with water to recover the BHMF dissolved in the aqueous layer (S210), a reverse fractionation method using water may be availed to remove a non-aqueous portion containing relatively high molecular weight oligomers among furan oligomers. In this method, BHMF and most low-molecular weight furan oligomers are dissolved in an aqueous fraction present at the upper portion while the relative polymers exist as resins in the lower fraction. BHMF and low-molecular weight furan oligomers dissolved in water can be recovered by dehydrating the aqueous layer, and the water recovered through the dehydration process can be reused. The amount of water fed for the fractionation may be 1- to 10-fold greater and particularly 2- to 5-fold greater than the weight of the low-molecular weight furan mixture obtained in the step of synthesizing a low-molecular weight furan mixture (S100). When water is fed in an amount less than the weight of the low-molecular weight furan mixture, the extraction and fractionation of BHMF may be degraded with the resultant failure of the reverse fractionation in providing a significant performance. The amount of water greater than the 10-fold weight of the low-molecular weight furan mixture enhances the efficiency of separating the low-molecular weight portion, but inevitably requires an increased volume of the fractionation tank and consumes much energy and time for dehydration, which is of no commercial significance.

In the step of adding an organic solvent to remove insoluble salt components (S220), a selective dissolution and filtration method taking advantage of a solubility difference may be applied to the removal of catalyst acid salts and levulinates. BHMF and furan oligomers are highly soluble in polar organic solvents whereas catalyst acid salts and levulinates exhibit very poor solubility and thus exist in a solid phase in polar organic solvents. Therefore, after the mixture is dissolved in an organic solvent, a salt fraction in a solid phase can be effectively separated by filtration. The BHMF and furan oligomers dissolved in the organic solvent can be recovered by removing the organic solvent through vacuum distillation of the aqueous layer. The distilled organic solvent can be reused. In this regard, the organic solvent is a polar solvent and particularly is selected from the low-molecular weight alcohol solvent group consisting of methanol, ethanol, propanol, isopropanol, and butanol, the low-molecular weight ketone solvent group consisting of acetone, butanone, pentanone, and methyl isobutyl ketone, or a combination thereof.

In the step of dissolving the mixture in an organic solvent, followed by cooling the solution to crystallization (S230), a crystallization process for enhancing BHMF purity may be utilized. When used, the two foregoing steps (S210 and S220) for high purification allows the production of BHMF monomers having a purity of 80% or higher. Because furan oligomers are contained therein, the impurities accounting for the residual 20% or less can be used as a polymer materials such as epoxy, etc. As needed, however, a crystallization process may be further employed for the production of BHMF monomers having a purity of 90% or higher.

Because BHMF and furan oligomers, although different in the number of the repeat unit, are common in taking a furan ring and a hydroxymethyl group in the principal structure thereof, it is difficult to selectively crystallize BHMF alone. Hence, in the sense of solubility selectivity, which is a principle for crystallization, the selection of suitable solvents which provide low solubility for BHMF and high solubility for furan oligomers has a critical influence on the crystallization efficiency. After extensive investigation into various commercially accessible solvents, the present inventors found that some ketone- or alcohol-based solvents have strengths on the solubility selectivity. After a mixture of BHMF and furan oligomers is fed into an organic solvent, a BHMF saturated solution is obtained in the condition of a medium temperature of 40° C. or higher. Upon heating at a temperature higher than 76° C., which is the melting point of BHMF, BHMF and the organic solvent may exist as a liquid mixture phase, depending on kinds of the solvent. Subsequently, cooling the saturated solution or liquid mixture allows the deposition of BHMF monomer crystals. Their purity increases relative to that before the crystallization. The organic solvent is particularly selected from the group consisting of methanol, ethanol, propanol, isopropanol, butanol, acetone, butanone, pentanone, methylisobutyl ketone, and a combination thereof, and more particularly selected from the group consisting of propanol, isopropanol, butanol, acetone, butanone, and a combination thereof. Typically, a higher input of the solvent relative to the fraction of a solid phase allows a higher BHMF purity after crystallization, but a lower recovery rate, and vice versa.

Below, a detailed description will be given of the method for producing BHMF of the present disclosure, with reference to the following Comparative Example and Examples.

Comparative Example 1

After furfuryl alcohol, formalin, and succinic acid were fed together into a reactor as indicated for relative weight ratios of the raw materials in Table 1, below, the raw materials were allowed to react with each other for 4 hours at atmospheric pressure while the temperature was maintained at 80° C. Thereafter, liquid-phase NaOH was fed in an amount of 2 molar ratios relative to the input of succinic acid to neutralize the reaction mixture. After being cooled to 60° C. and depressurized to 100 torr, the reaction mixture was dehydrated.

Example 1 (Synthesis of Low-Molecular Weight Furan Mixture)

After furfuryl alcohol, paraformaldehyde, and succinic acid were fed together into a reactor as indicated for relative weight ratios of the raw materials in Table 1, below, the raw materials were allowed to react with each other for 4 hours at atmospheric pressure while the temperature was maintained at 120° C. Subsequently, liquid phase NaOH was fed in an amount of 2 molar ratios relative to the input of succinic acid to neutralize the reaction mixture. The reaction mixture was cooled to 60° C. and depressurized to 100 torr before dehydration. After completion of the reaction, unreacted furfuryl alcohol was recovered while the temperature and the pressure were maintained at 120° C. and 100 torr, respectively. Finally, a reddish brown viscous liquid fraction was recovered. In nature, BHMF exists as a solid phase at room temperature. Since furan structure-based liquid impurities is soluble in BHMF, the low-molecular weight furan mixture was recovered as a liquid phase.

TABLE 1

| | Comparative Example 1 | Example 1 |
|---|---|---|
| Input raw material - Relative weight ratio | Furfuryl alcohol- 100 Formalin (37%)- 165 Succinic acid- 0.5 | Furfuryl alcohol- 100 Paraformaldehyde (91%)- 3.5 Succinic acid- 0.2 |
| Reaction condition | 80° C., 1 bar, 4 hr | 120° C., 1 bar, 4 hr |
| Catalyst neutralization | ○ | ○ |
| Dehydration | ○ | ○ |
| Furfuryl alcohol recovery | X | ○ |
| Content in Reaction mixture (GPC area %) | BHMF 16.6% Levulinic acid 40.4% Furfuryl alcohol 36.7% The others 6.3% | BHMF 51.0% Levulinic acid 5.1% Furfuryl alcohol 11.5% The others 32.4% |
| BHMF/Levulinic acid Ratio | 0.41 | 10 |

Figure 4:
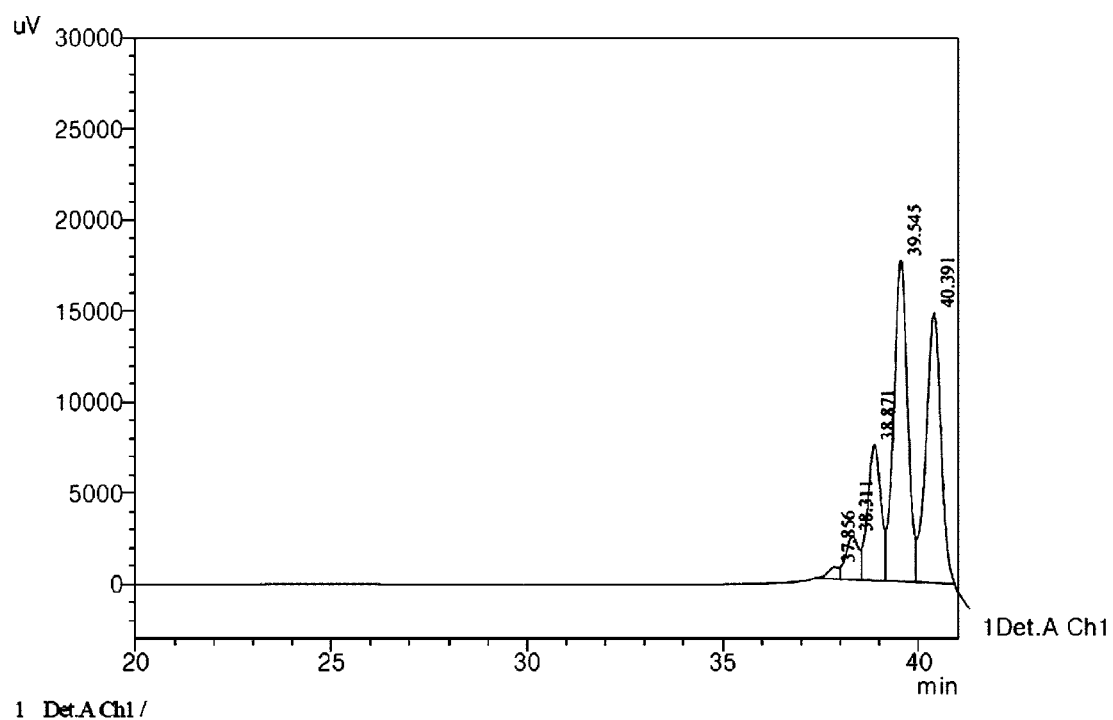
FIG. 4 is a GPC chromatogram of the low-molecular weight furan mixture prepared according to Comparative Example 1 in the present disclosure, with GPC data recorded therein.
Figure 5:
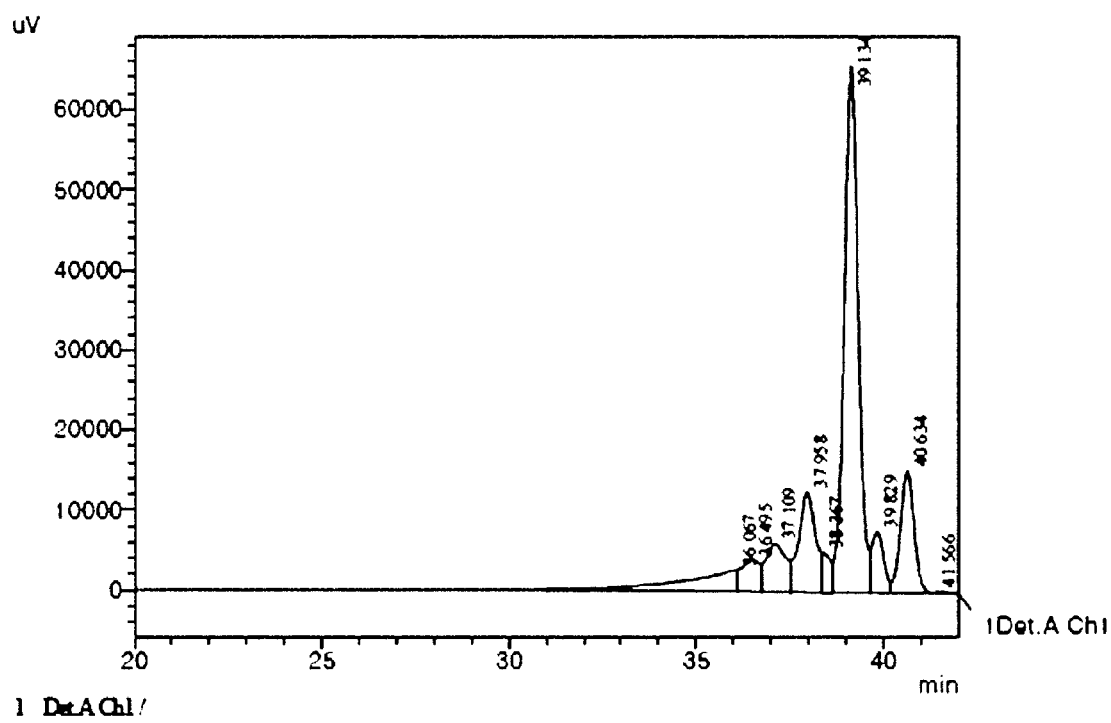
FIG. 5 is a GPC chromatogram of the low-molecular weight furan mixture prepared according to Example 1 in the present disclosure, with GPC data recorded therein.

FIG. 4 is a GPC chromatogram of the low-molecular weight furan mixture prepared according to Comparative Example 1 in the present disclosure, with GPC data recorded therein. FIG. 5 is a GPC chromatogram of the low-molecular weight furan mixture prepared according to Example 1 in the present disclosure, with GPC data recorded therein. Respective samples from the reaction products according to Comparative Example and Example 1 were dissolved at 2.5 wt % in THF before GPC analysis (Shimadzu, Gel Permeation Chromatography Systems; Shodex, KF-801, 802, 803, and 805 Columns) with tetrahydrofuran (HPLC grade) used as a mobile phase at a flow rate of 1 ml/min and at an analysis temperature of 40° C.

Referring to FIG. 4 and Table 1, the analysis result shows that the sample from the low-molecular weight furan mixture obtained according to Comparative Example 1 had a significantly high concentration of levulinic acid (RT=39.5 min, 40.4 area %), and a relative small amount of the target material BHMF (RT=38.9 min, 16.6 area %), indicating that when formalin was used as a raw material, contact with water causes furfuryl alcohol to predominantly undergo conversion to levulinic acid over the target reaction hydroxymethylation. In Comparative Example 1, a significant amount of residual furfuryl alcohol was also detected since unreacted furfuryl alcohol was not recovered (RT=40.4 min, 36.7 area %).

With reference to FIG. 5 and Table 1, the analysis result shows that the target material BHMF occupied the larger half of the sample from the low-molecular weight furan mixture obtained according to Example 1 (RT=39.1 min, 51.0 area %). Levulinic acid, which was detected in a significant amount in Comparative Example, was greatly reduced in Example 1 (RT=39.8 min, 5.1%). These data imply that when paraformaldehyde is used, contact with water is minimized so that the target hydroxymethylation predominantly occurs than conversion to levulinic acid. Since unreacted furfuryl alcohol was recovered, the content of residual furfuryl alcohol was reduced in Example 1 (RT=40.6 min, 11.5 area %).

Example 2 (Removal of Impurities from Low-Molecular Weight Furan Mixture)

Impurities present in the low-molecular weight furan mixture synthesized in Example 1 were removed as follows: first, reverse fractionation using water was conducted in order to remove a non-aqueous portion containing high-molecular weight oligomers. Water was added in an amount four-fold larger than the weight of mixture, followed by stirring for 15 min at room temperature to set a condition under which BHMF could be dissolved in water. Thereafter, the mixture was poured to a separatory funnel and left to stand for 30 min to allow fractionation. A yellow aqueous BHMF solution was located in the upper portion of the separatory funnel while a non-aqueous polymer furan mixture appeared reddish brown in the lower portion of the separatory funnel. The upper and the lower layer were separated and the upper aqueous BHMF layer alone was used in subsequent processes.

Then, the recovered aqueous BHMF solution was dehydrated. In the reactor, the aqueous BHMF solution was dehydrated at 60° C. and 100 torr while being stirred. The condition of 80° C. and 30 torr was applied within as short as the last 30 min of the dehydration so that even a trace amount of moisture was removed. As the BHMF monomers recovered after dehydration were cooled to a temperature below the melting point 76° C., the monomers were crystallized and existed as a solid phase at room temperature.

Additionally, the BHMF monomers were dissolved at a weight ratio of 1:3 of acetone to remove the catalyst acid salts and levulinates that were present in trace amounts therein. Stirring for 30 min at about 30° C. completely dissolved the BHMF monomers while the catalyst acid salts and levulinates existed as suspended matter. The suspended matter was removed by vacuum filtration with a filter put on the Buchner funnel, and the BHMF monomer fraction in acetone was recovered. The recovered solution was completely dried through the distillation of acetone, with the consequent recovery of yellow solid-phase BHMF monomers.

Figure 6:
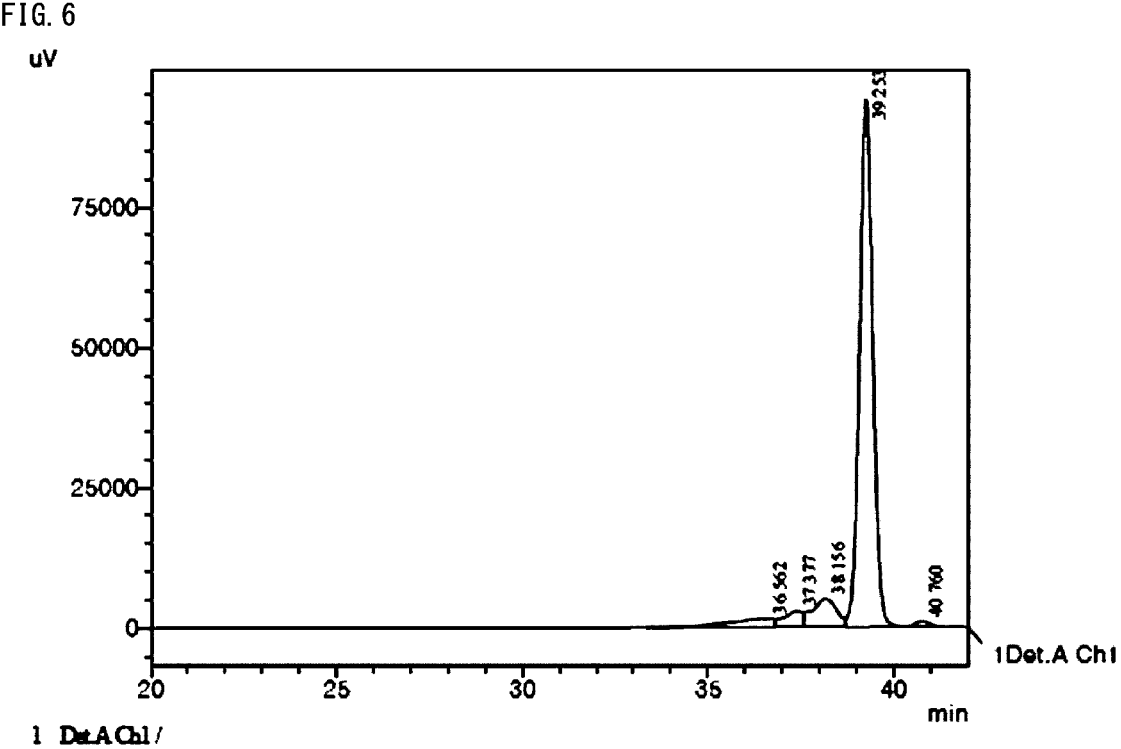
FIG. 6 is a GPC chromatogram of the BHMF prepared according to Example 2 in the present disclosure, with GPC data recorded therein.

FIG. 6 is a GPC chromatogram of the BHMF prepared according to Example 2 in the present disclosure, with GPC data recorded therein. A 2.5 wt % solution of BHMF obtained according to Example 2 in THF was subjected to GPC instrumental analysis (Shimadzu, Gel Permeation Chromatography Systems; Shodex, KF-801, 802, 803, 805 Columns). At an analysis temperature of 40° C., tetrahydrofuran (HPLC grade) was used as a mobile phase at a flow rate of 1 ml/min.

With reference to FIG. 6, the analysis result of the BHMF recovered according to Example 2 shows that the target material BHMF predominates in the sample (RT=39.2 min, 82.4 area %). Almost all of the polymer fraction was removed and the residual unreacted furfuryl alcohol in the low-molecular weight furan mixture was also eliminated in the fractionation and dehydration processes and observed to be present at a content less than 1%.

Example 3 (BHMF Crystallization)

Crystallization of the BHMF monomers obtained in Example 2 enhanced the purity of BHMF. Addition of acetone at a weight ratio of 0.5 to BHMF monomers was followed by stirring at 55° C. for 30 min. After stirring, a liquid-phase BHMF-acetone solution was recovered and then cooled to 25° C. while stirring. The stirring was continued for 6 hours with the temperature maintained. Highly pure BHMF in a powder phase was deposited with the cooling of the solution and increasingly increased in output with the continuation of stirring. The highly pure, powdery BHMF was recovered by vacuum filtration with a filter put on a Buchner funnel. The acetone solution passing through the filter was separately collected for reuse. In the condition of vacuum filtration, the BHMF powder was exposed for a short time to and coated with a small amount of acetone for primary wash. Subsequently, the BHMF powder was surface washed with n-hexane to remove the acetone solution from the surface thereof. Finally, highly pure, off-white BHMF powder was obtained and dried for 1 hour in a 60° C. oven before instrumental analysis.

Figure 7:
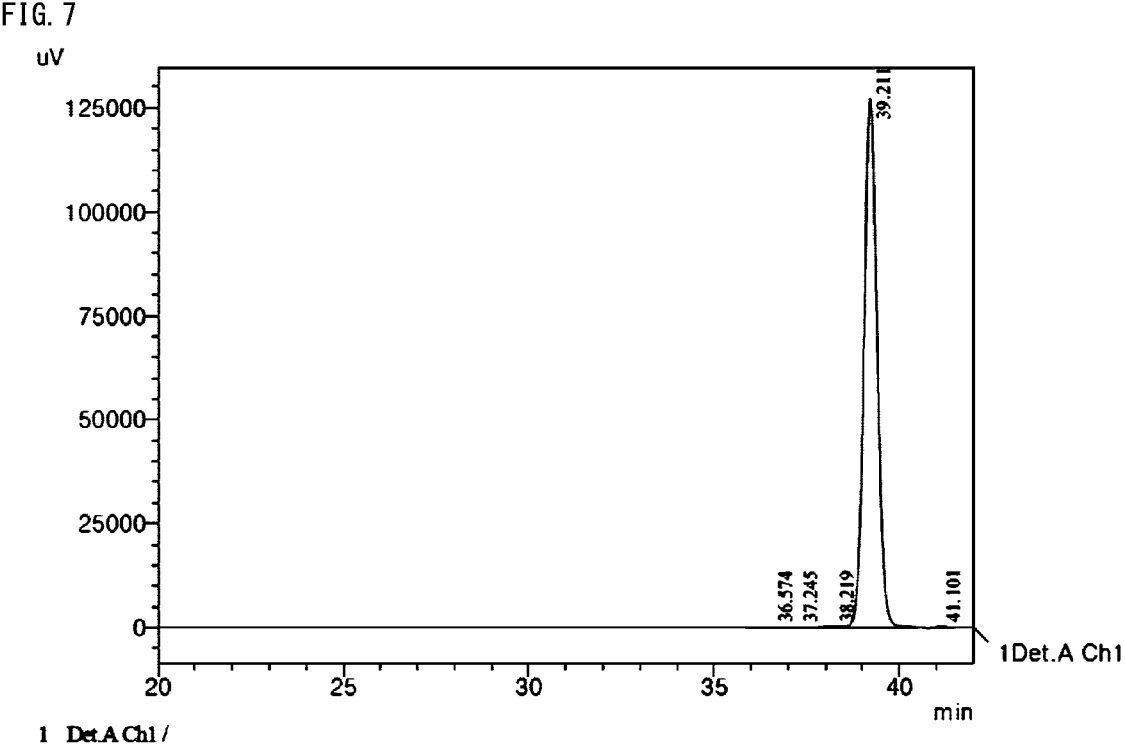
FIG. 7 is a GPC chromatogram of the BHMF prepared according to Example 3 in the present disclosure, with GPC data recorded therein.

FIG. 7 is a GPC chromatogram of the BHMF prepared according to Example 3 in the present disclosure, with GPC data recorded therein. A 2.5 wt % solution of BHMF obtained according to Example 3 in THF was subjected to GPC instrumental analysis (Shimadzu, Gel Permeation Chromatography Systems; Shodex, KF-801, 802, 803, 805 Columns). At an analysis temperature of 40° C., tetrahydrofuran (HPLC grade) was used as a mobile phase at a flow rate of 1 ml/min.

Referring to FIG. 7, the analysis result shows that the BHMF was highly purified (RT=39.2 min, 99.7 area %).

Figure 8:
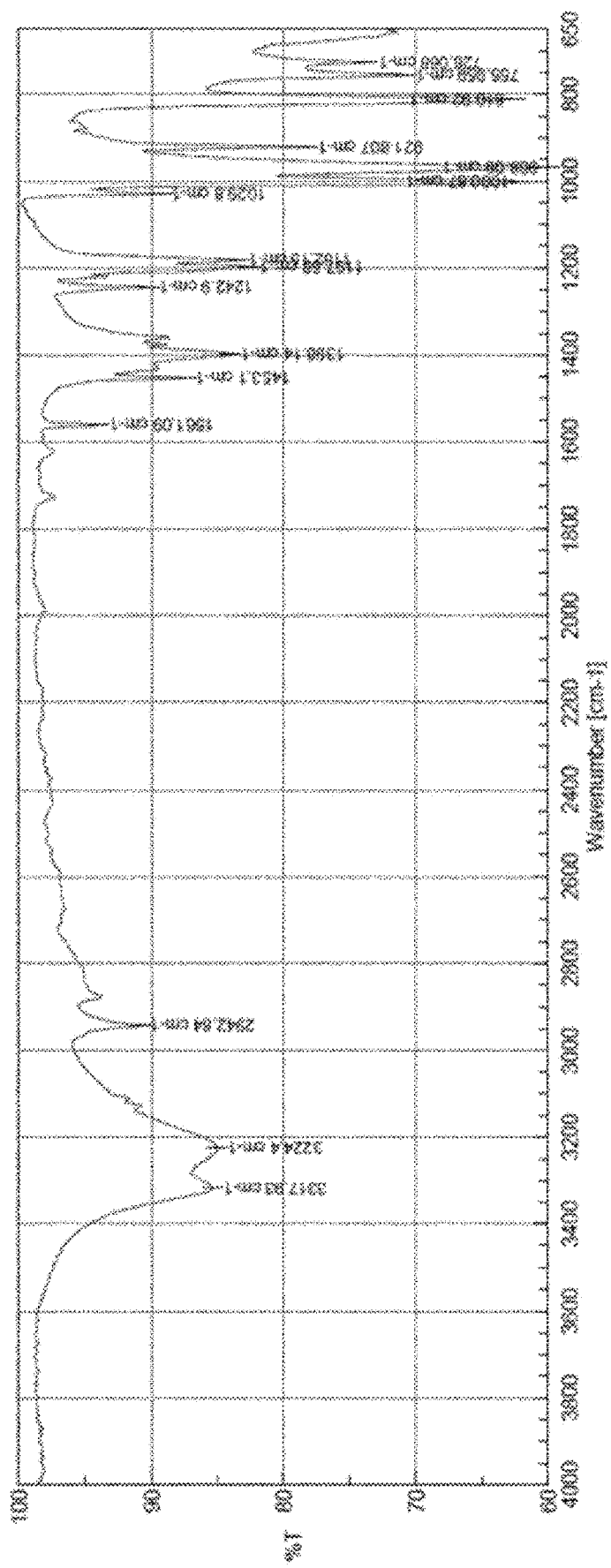
FIG. 8 is a FTIR spectrum of the highly pure BHMF prepared according to Example 3 in the present disclosure.

FIG. 8 is a FTIR spectrum of the highly pure BHMF prepared according to Example 3 in the present disclosure.

Referring to FIG. 8, FT-IR instrumental analysis (Jasco, FT/IR-4100) data for the highly pure BHMF are as follows.

FT-IR (equipped with ATR accessory): 3318, 3224, 2943, 1561, 1453, 1398 cm-1

Figure 9:
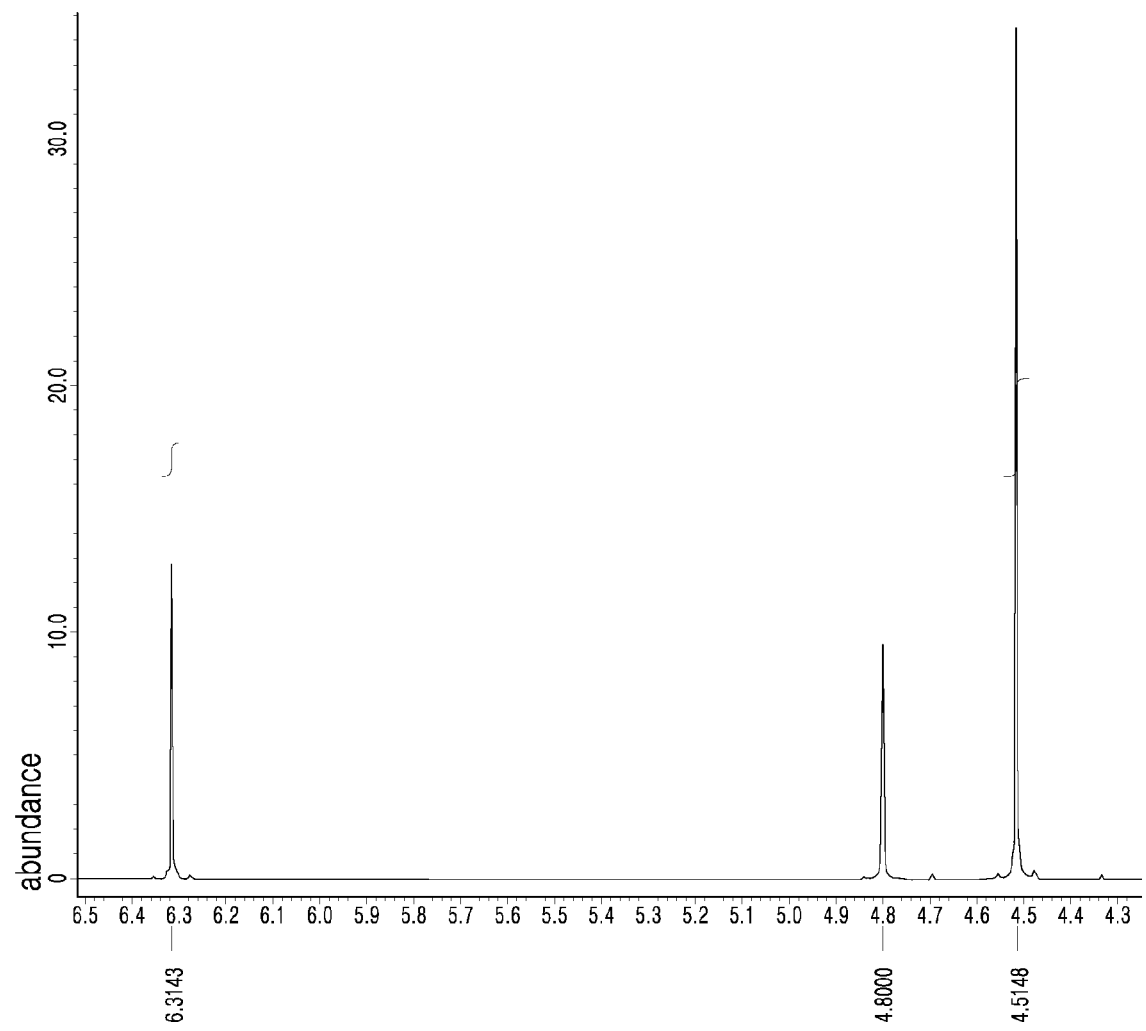
FIG. 9 is a 1H NMR spectrum of the highly pure BHMF prepared according to Example 3 in the present disclosure.

FIG. 9 is a 1H NMR spectrum of the highly pure BHMF prepared according to Example 3 in the present disclosure.

Referring to FIG. 9, 1H NMR instrumental analysis data for the highly pure BHMF are as follows.

1H NMR (400 MHz, D20): δ 6.31 (s, 2H), 4.51 (s, 4H);

FIG. 10 shows GS-MS data of the highly pure BHMF prepared according to Example 3 in the present disclosure. A 0.2 wt % solution of the highly pure BHMF obtained in Example 3 in THF was subjected to GC-MS instrumental analysis (Shimadzu, GCMS-QP5050; SGE Analytical Science, BP5 Column).

With reference to FIG. 10, the highly pure BHMF prepared according to Example 3 was found to have a molecular weight of 128, identical to the value known in previous documents, as measured by GC/MS instrumental analysis.

Meanwhile, an experiment was conducted to examine whether a reaction temperature range has an influence on the synthesis of the low-molecular weight furan mixture in Example 1. That is, an examination was made to see whether or not the temperature range of 100° C. to 150° C. in which the step of hydroxymethylating furfuryl alcohol (S110) is conducted as described above is useful for the stability of the raw material furfuryl alcohol and suitable for effectively controlling the amount of by-products. Requiring a temperature of 100° C. or higher, the hydroxymethylation of furfuryl alcohol is accompanied by the generation of some by-products such as high-molecular weight furan polymers, etc.

Example 4 (Generation of by-Product According to Reaction Temperature)

Furfuryl alcohol was fed, together with 3 phr (parts per hundred resin) of succinic acid, into a reactor the inner temperature of which was then elevated at a rate of 20° C./hr while stirring the reactants. Polymerization occurred by self-condensation with the elevation of temperature in the reactor, and the furfuryl alcohol turned dark in color.

Figure 11:
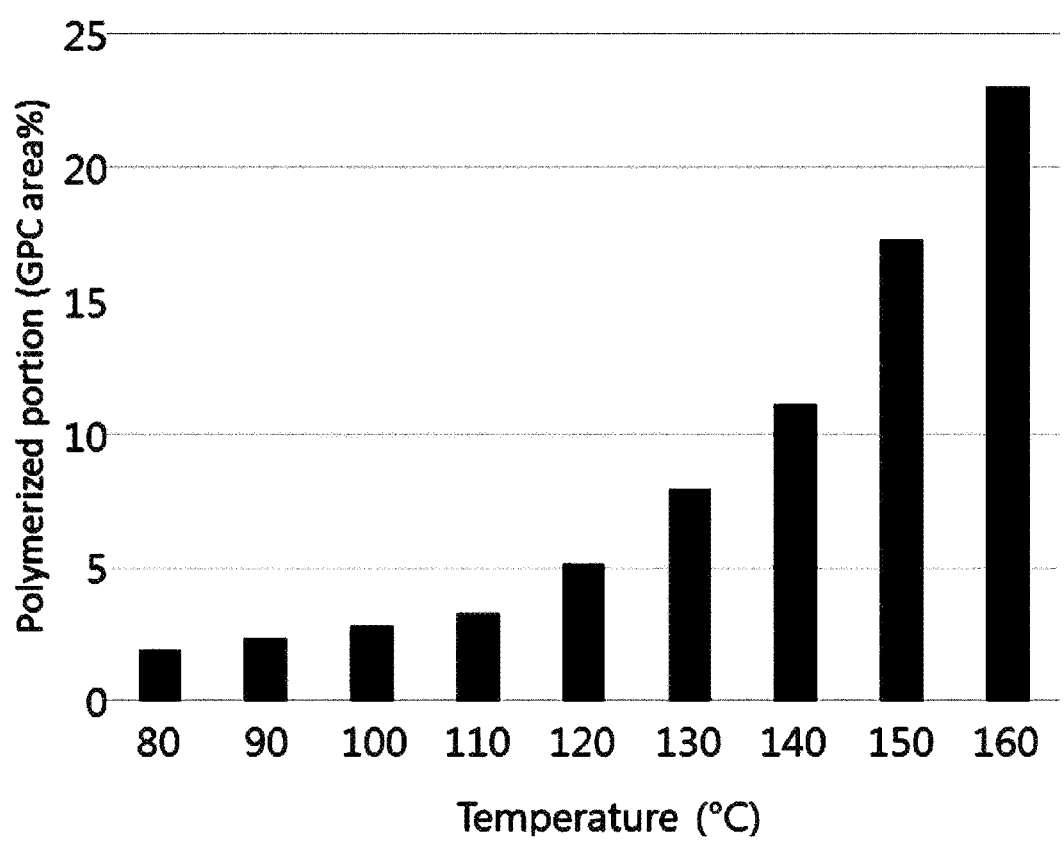
FIG. 11 is a graph showing amounts of by-products versus reaction temperatures.

FIG. 11 is a graph showing amounts of by-products versus reaction temperatures. That is, FIG. 11 explains the effect of reaction temperatures on the stability of furfuryl alcohol. Samples were taken from the material prepared in Example 4 at regular intervals of 10° C. in the temperature section from 80° C. to 160° C. and each of the samples was subjected to GPC analysis to quantify by-products. For GPC instrumental analysis (Shimadzu, Gel Permeation Chromatography Systems; Shodex, KF-801, 802, 803, 805 Columns), the samples were dissolved in an amount of 2.5 wt % in THF. At an analysis temperature of 40° C., tetrahydrofuran (HPLC grade) was used as a mobile phase at a flow rate of 1 ml/min.

With reference to FIG. 11, the temperature range of 100° C. to 150° C. was observed to effectively control the generation of by-products as the output of by-products was measured to be 20% or less relative to the input of furfuryl alcohol. Particularly, the output of by-products was 5% relative to the input of furfuryl alcohol in the temperature range of 100° C. to 120° C. which was thus identified to very effectively control the generation of by-products. More than 20% of by-products was detected at 160° C. or higher. When the hydroxymethylation of furfuryl alcohol was maintained for the typical time 2 hours or longer at a temperature exceeding 150° C., the reaction mixture increased in viscosity and temperature by gelation and turned into a recovery-impossible solid phase.

Meanwhile, an experiment was conducted to examine whether pKa range of the acid catalysts selected have an influence on the synthesis of the low-molecular weight furan mixture in Example 1. Requiring an acid catalyst, the hydroxymethylation of furfuryl alcohol is accompanied by the generation of some by-products such as high-molecular weight furan polymers, etc. In Example 5, the stability of the raw material furfuryl alcohol was identified according to acid catalysts and pKa ranges of the catalysts in which the generation of by-products can effectively controlled are shown.

Example 5 (Measurement of Output of by-Product According to Acid Catalyst)

Furfuryl alcohol (referred to as "FA" in Table 2, below) was fed, together with 3 phr of each of the acid catalysts listed in Table 2), into a glass vessel which was then hermitically sealed and exposed for 90 min to a 90° C. oven. As the reactant was exposed to the acid catalysts, polymerization occurred and furfuryl alcohol turned dark in color. Some of the mixture was gelled to solidification.

The samples were cooled to room temperature and subjected to GPC analysis to quantify by-products. For GPC instrumental analysis (Shimadzu, Gel Permeation Chromatography Systems; Shodex, KF-801, 802, 803, 805 Columns), the samples were dissolved in an amount of 2.5 wt % in THF. At an analysis temperature of 40° C., tetrahydrofuran (HPLC grade) was used as a mobile phase at a flow rate of 1 ml/min.

In order to test the generation of by-products and the stability of the raw material according to pKa of acid catalysts, Example 5 employed 3 phr of the acid catalysts, which is greater than the amount of the acid catalysts in Example 1. However, an acid catalyst may be fed in an amount of 0.05 phr to 0.3 phr relative to furfuryl alcohol upon the practical preparation of the low-molecular weight furan mixture, as described above.

As is understood from the data of Table 2, the output of by-products in the presence of an acid catalyst with a pKa of 4.0 or higher was 10% relative to the input of furfuryl alcohol. For the sample to which 3 phr of citric acid having a pKa of 3.13 was applied, the output of by-products was increased. However, because the acid catalyst is used in an amount of 0.05 phr to 0.3 phr relative to furfuryl alcohol upon the practical preparation of the low-molecular weight furan mixture according to the present disclosure, the content of by-products will be less than 26.8%. Hence, citric acid can also be used as an acid catalyst according to the present disclosure. On the other, oxalic acid and phosphoric acid, which both have a pKa less than 4.0, causes complete gelation, making recovery and GPC analysis impossible (by-product content ~100%).

TABLE 2

| | Acid catalyst (pKa) | | | | | |
|---|---|---|---|---|---|---|
| | Oxalic acid (1.25) | Phosphoric acid (2.15) | Citric acid (3.13) | Succinic acid (4.21) | Monosodium succinate (5.41) | Disodium citrate (6.40) |
| Relative Wt ratio | FA- 100 Acid catalyst-3 | FA- 100 Acid catalyst-3 | FA- 100 Acid catalyst-3 | FA- 100 Acid catalyst-3 | FA-100 Acid catalyst-3 | FA- 100 Acid catalyst-3 |
| Rxn Condition | 90° C., 1 bar, 1.5 hr | 90° C., 1 bar, 1.5 hr | 90° C., 1 bar, 1.5 hr | 90° C., 1 bar, 1.5 hr | 90° C., 1 bar, 1.5 hr | 90° C., 1 bar, 1.5 hr |
| By-product content | ~100% | ~100% | 26.8% | 6.9% | 1.8% | 0.5% |
| Phase | Gel | Gel | Liquid | Liquid | Liquid | Liquid |

The features, structures, effects, and the like described in the above-described embodiments include at least one embodiment of the present invention, but the present invention is not limited only to one embodiment. Further, the features, structures, effects, and the like illustrated in each embodiment may be combined or modified to other embodiments by those skilled in the art. Therefore, contents related to the combination or the modification should be interpreted to be included in the scope of the invention.

In addition, while the present invention has been particularly described with reference to exemplary embodiments, the present invention is not limited thereto. It will be understood by those skilled in the art that various modifications and applications, which are not illustrated in the above, may be made without departing from the spirit and scope of the present invention. For example, each component illustrated in the embodiments may be modified and made. It should be interpreted that differences related to these modifications and applications are included in the scope of the invention defined in the appended claims.

In various embodiments of the present disclosure, a furan monomer having a bifunctional hydroxymethyl group, such as BHMF, can be very easily synthesized using furfuryl alcohol based on a biomass-derived pentose. The BHMF production method according to various embodiments of the present disclosure is industrially valuable because the method utilizes an industrially highly accessible raw material in effectively producing BHMF. Subsequently, the method can play a critical role in commercializing various derived furan products using BHMF as a raw material. In the sense that the BHMF production method is based on non-edible biomass or waste biomass, an environmental effect of reducing petroleum consumption is also expected.

What is claimed is:

1. A method of preparing 2, 5-bis(hydroxymethyl) furan (BHMF), the method comprising:
    converting furfuryl alcohol to a low-molecular weight furan mixture containing BHMF in an amount of 51 wt % or greater relative to a total weight of the low-molecular weight furan mixture; and
    extracting and purifying a furan monomer having a bifunctional hydroxymethyl group from the low-molecular weight furan mixture,
    wherein the converting comprises hydroxymethylating the furfuryl alcohol by mixing the furfuryl alcohol, formaldehyde, and an acid catalyst,
    wherein the furfuryl alcohol is mixed at a 6- to 15-fold greater molar ratio to the formaldehyde,
    wherein the method further comprises recovering unreacted furfuryl alcohol which has not undergone hydroxymethylation, and
    wherein the extracting and purifying comprises:
        fractionating the low-molecular weight furan mixture with water to recover the BHMF dissolved in an aqueous layer;
        adding an organic solvent to the low-molecular weight furan mixture to remove insoluble salt components from the low-molecular weight furan mixture; and
        dissolving the low-molecular weight furan mixture in the organic solvent to provide a solution, followed by cooling the solution to crystallization.

2. The method of claim 1, wherein the formaldehyde comprises paraformaldehyde.

3. The method of claim 2, wherein the hydroxymethylating allows the furfuryl alcohol to be associated with monomeric formaldehyde produced by thermal degradation of the paraformaldehyde.

4. The method of claim 1, wherein the hydroxymethylating is conducted at a temperature of 100° C. to 150° C.

5. The method of claim 1, wherein the acid catalyst is mixed in an amount of 0.05 phr to 0.3 phr relative to the furfuryl alcohol.

6. The method of claim 1, wherein the acid catalyst is an organic acid with a pKa of 3.0 to 6.4 and is selected from the group consisting of acetic acid, acetoacetic acid, adipic acid, azelaic acid, benzoic acid, citric acid, cyclohexanecarboxylic acid, enolpyruvic acid, formic acid, fumaric acid, galactaric acid, galactonic acid, glucaric acid, gluconic acid, glutaric acid, glyceric acid, glyceric acid 2-phosphate, glycolic acid, glyoxylic acid, hydroxybutyric acid, isobutyric acid, isophthalic acid, itaconic acid, lactic acid, levulinic acid, malic acid, methyl malonic acid, pimelic acid, succinic acid, suberic acid, tartaric acid, terephthalic acid, monosodium succinate, disodium citrate, and a combination thereof.

7. A method of preparing 2, 5-bis(hydroxymethyl) furan (BHMF), the method comprising:
    converting furfuryl alcohol to a low-molecular weight furan mixture; and
    extracting and purifying a furan monomer having a bifunctional hydroxymethyl group from the low-molecular weight furan mixture,
    wherein the extracting and purifying comprises:
        fractionating the low-molecular weight furan mixture with water to recover the BHMF dissolved in an aqueous layer;
        adding an organic solvent to the low-molecular weight furan mixture to remove insoluble salt components from the low-molecular weight furan mixture; and
        dissolving the low-molecular weight furan mixture in the organic solvent to provide a solution, followed by cooling the solution to crystallization.

8. The method of claim 7, wherein the fractionating is conducted by adding water at a 1- to 10-fold greater weight ratio relative to the low-molecular weight furan mixture and recovering the BHMF dissolved in the aqueous layer.

9. The method of claim 7, wherein the organic solvent is a polar solvent configured to selectively dissolve BHMF and is selected from a low-molecular weight alcohol solvent group consisting of methanol, ethanol, propanol, isopropanol, and butanol, a low-molecular weight ketone solvent group consisting of acetone, butanone, pentanone, and methyl isobutyl ketone, or a combination thereof.

* * * * *